US009924715B2

(12) United States Patent
Zotkin et al.

(10) Patent No.: US 9,924,715 B2
(45) Date of Patent: Mar. 27, 2018

(54) ZINC OR COPPER (II) SALT AND USE THEREOF AS A BIOCIDE

(71) Applicant: LABORATORIYA BIO ZET, LLC, Moscow (RU)

(72) Inventors: Igor I. Zotkin, Nizhny Novgorod (RU); Nadezhda V. Kuznetsova, Nizhny Novgorod (RU); Larisa V. Kabanova, Nizhny Novgorod (RU); Nikolay N. Nosik, Moscow (RU); Dmitriy N. Nosik, Moscow (RU)

(73) Assignee: LABORATORIYA BIO ZET, LLC, Moscow (RU)

( * ) Notice: Subject to any disclaimer, the term of this patent is extended or adjusted under 35 U.S.C. 154(b) by 0 days.

(21) Appl. No.: 15/459,693

(22) Filed: Mar. 15, 2017

(65) Prior Publication Data

US 2017/0238545 A1   Aug. 24, 2017

Related U.S. Application Data

(63) Continuation of application No. PCT/RU2015/000564, filed on Sep. 7, 2015.

(30) Foreign Application Priority Data

Sep. 16, 2014 (RU) .................................. 2014137615

(51) Int. Cl.
| A01N 37/06 | (2006.01) |
| A01N 37/02 | (2006.01) |
| C07C 57/04 | (2006.01) |
| C07C 57/08 | (2006.01) |
| C07C 53/124 | (2006.01) |
| C07C 53/126 | (2006.01) |
| C07C 53/122 | (2006.01) |
| C07C 57/10 | (2006.01) |
| C07C 57/03 | (2006.01) |

(52) U.S. Cl.
CPC ............. *A01N 37/06* (2013.01); *A01N 37/02* (2013.01); *C07C 53/122* (2013.01); *C07C 53/124* (2013.01); *C07C 53/126* (2013.01); *C07C 57/03* (2013.01); *C07C 57/04* (2013.01); *C07C 57/08* (2013.01); *C07C 57/10* (2013.01)

(58) Field of Classification Search
CPC .................................. A01N 37/02; A01N 37/06
See application file for complete search history.

(56) References Cited

U.S. PATENT DOCUMENTS

| 4,258,090 A | 3/1981 | Moraru |
| 5,185,033 A | 2/1993 | Hani et al. |
| 5,298,061 A | 3/1994 | Waldron et al. |
| 5,460,644 A | 10/1995 | Thomassen |
| 5,508,350 A | 4/1996 | Cadorniga et al. |
| 5,540,954 A | 7/1996 | Nicholas et al. |
| 5,717,007 A | 2/1998 | Cambon |
| 6,399,560 B1 | 6/2002 | Kwon et al. |
| 6,858,658 B2 | 2/2005 | Tomasgaard et al. |
| 7,410,553 B2 | 8/2008 | Blanpied et al. |
| 2008/0219944 A1 | 9/2008 | Longo et al. |
| 2009/0223408 A1 | 9/2009 | Richardson et al. |
| 2012/0202153 A1 | 8/2012 | Hatakeyama |

FOREIGN PATENT DOCUMENTS

| EP | 2161316 A1 | 3/2010 | |
| EP | 2360214 A1 | 8/2011 | |
| JP | 54060346 | 5/1979 | |
| JP | 2000273365 A | 10/2000 | |
| JP | 2000273366 A | 10/2000 | |
| JP | 2001172548 A | 6/2001 | |
| JP | 2006-176785 | * 7/2006 | .......... C09D 133/02 |
| RU | 2315793 C1 | 1/2008 | |
| RU | 2378363 C1 | 1/2010 | |
| RU | 2497857 C1 | 11/2013 | |
| WO | 2007026692 A1 | 3/2007 | |
| WO | 2013108880 A1 | 7/2013 | |

OTHER PUBLICATIONS

International Search Report from International Application No. PCT/RU2015/000564, filed Sep. 7, 2015, dated Nov. 18, 2015.
Guidelines for investigating and evaluating the virucidal activity of disinfectants MU 3.5.24.31-08, Dec. 13, 2008.
Chemical Abstracts Service CAS on STN RN 299410-54-1, entered on Oct. 26, 2000.
Chemical Abstracts Service CAS on STN RN 299217-78-0, entered on Oct. 25, 2000.
Chemical Abstracts Service CAS on STN RN 299217-75-7, entered on Oct. 25, 2000.
Chemical Abstracts Service CAS on STN RN 299217-73-5, entered on Oct. 25, 2000.
Chemical Abstracts Service CAS on STN RN 299216-77-6, entered on Oct. 25, 2000.

(Continued)

*Primary Examiner* — Joseph R Kosack
(74) *Attorney, Agent, or Firm* — Patentbar International, P.C.

(57) ABSTRACT

Zinc and copper (II) salts of the general formula $CH_2=C(R^1)COO-M-OCOR^2$ are disclosed, wherein M-Zn or Cu, $R^1$—H or $CH_3$, $R^2$—$C_2$-$C_{25}$ alkyl, or $R^2$—CO—O— group is crotonate, or sorbate, or linoleate, excluding the compounds: $CH_2=C(CH_3)-COO-Zn-O-CO-C_2H_5$, $CH_2=CH-COO-Zn-O-CO-C_2H_5$, $CH_2=CH-COO-Cu-O-CO-C_2H_5$, $CH_2=C(CH_3)-COO-Zn-O-CO-(CH_2)_4-CH_3$, $CH_2=CH-COO-Zn-O-CO-(CH_2)_4-CH_3$, $CH_2=CH-COO-Zn-O-CO-(CH_2)_6-CH_3$, $CH_2=C(CH_3)-COO-Zn-O-CO-(CH_2)_6-CH_3$, $CH_2=CH-COO-Cu-O-CO-(CH_2)_6-CH_3$, $CH_2=CH-COO-Zn-O-CO-(CH_2)_{14}-CH_3$, $CH_2=C(CH_3)-COO-Zn-O-CO-(CH_2)_{16}-CH_3$, $CH_2=C(CH_3)-COO-Zn-O-CO-iso-C_{17}H_{35}$, $CH_2=CH-COO-Zn-O-CO-iso-C_{17}H_{35}$, $CH_2=C(CH_3)-COO-Zn-O-CO-(CH_2)_{17}-CH_3$.
Salts of the general formula wherein $R^2$—$C_2$-$C_{25}$ alkyl, or $R^2$—CO—O— group is crotonate, or sorbate, or linoleate, are applicable as biocides.

2 Claims, No Drawings

(56) References Cited

OTHER PUBLICATIONS

Chemical Abstracts Service CAS on STN RN 299216-70-9, entered on Oct. 25, 2000.
Chemical Abstracts Service CAS on STN RN 299216-72-1, entered on Oct. 25, 2000.
Chemical Abstracts Service CAS on STN RN 561007-33-8, entered on Aug. 3, 2003.
Chemical Abstracts Service CAS on STN RN 299424-34-3, entered on Oct. 26, 2000.
Chemical Abstracts Service CAS on STN RN 299424-33-2, entered on Oct. 26, 2000.

* cited by examiner

ZINC OR COPPER (II) SALT AND USE THEREOF AS A BIOCIDE

RELATED APPLICATIONS

This Application is a Continuation application of International Application PCT/RU2015/000564, filed on Sep. 7, 2015, which in turn claims priority to Russian Patent Application RU2014137615, filed Sep. 16, 2014, all of which are incorporated herein by reference in their entirety.

FIELD OF THE INVENTION

The invention relates to new chemical compounds—zinc and copper salts with organic acids which can find application as biocides.

BACKGROUND OF THE INVENTION

Various zinc and copper compounds exhibiting biocidal activity are known in the art, in particular, zinc and copper oxides and inorganic salts (U.S. Pat. No. 5,540,954, A01N 59/16, A01N 59/20, B27K 3/52, B05D 07/06, A01N 31/08, A01N 31/00, 1996; U.S. Pat. No. 6,858,658, A01N 59/20, A01N 59/16, C09D 5/16, C08K 03/10, C08K 03/18, C08K 03/22, 2005; US 20080219944, C09D 5/16, 2008; US 20090223108, C09D 5/16, C09D 5/14, 2009), zinc and copper naphthenates or resinates (EP 2161316, C09D 133/06, C09D 133/12, C09D 143/04, C09D 5/16, C09D 7/12, 2010; EP 2360214, C09D 143/04, C09D 193/04, C09D 5/16, 2011; U.S. Pat. No. 4,258,090, C04B 41/45, C04B 41/52, C04B 41/60, C04B 41/70, B05D 03/02, 1981), ammonia complexes of zinc salts (U.S. Pat. No. 5,460,644, C08K 3/10, C08K 3/00, C09D 5/14, C09D 5/00, 1995), zinc and copper pyrithionates—bis-(2-(pyridylthio)-1,1'-dioxides (U.S. Pat. No. 5,185,033, C09D 5/14, C09D 5/16, 1993; U.S. Pat. No. 5,298,061, C09D 5/16, C09D 5/14, 1994; U.S. Pat. No. 5,717,007, C09D 5/16, C08L 33/10, C08K 05/17, C08K 05/18, 1998; U.S. Pat. No. 6,399,560, A01N 43/40, A01N 43/34, A61L 2/18, C11D 3/48, 2002; U.S. Pat. No. 7,410,553, D21C 5/02, B32B 27/04, D21G 1/02, 2008). The above mentioned compounds were used with various degrees of efficiency as additives to coatings intended for treatment of building structures, prevention of underwater structures and ship parts from fouling as well as paper and wood treatment.

Zinc salt with acetic and methacrylic acids, i.e. zinc methacrylate-acetate (hereinafter referred to as ZMA) exhibiting a certain biocidal activity when compounded with aqueous styrene-acrylic dispersion being used as polymer pruner for applying paint coatings to various surfaces is also known (RU 2315793, C09D 5/14, C09D 131/02, C09D 133/10, 2008).

The closest analogues of the proposed compounds are zinc or copper (II) salts with two acids one of which is acrylic or methacrylic acid and the other is aliphatic carboxylic acid selected from the group including propionic, capronic (hexanoic), caprilic (octanoic), palmitic (hexadecanoic), linolic (octadecadienoic), oleic (octadecenoic), stearic (octadecanoic), nonadecanoic acids. The above compounds are known from ACS on STN (RN 71502-44-8, 177957-21-0, 299216-74-3, 299216-75-4, 299410-52-9, 299217-71-3, 299410-54-1, 299217-78-0, 299217-75-7, 299217-73-5, 299216-77-6, 299216-70-9, 299216-72-1, 561007-33-8) and can be described by the general formula:

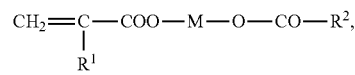

wherein M-Zn or Cu,
$R^1$—H or $CH_3$,
$R^2$—$C_2H_5$, $C_5H_{11}$, $C_7H_{15}$, $C_{15}H_{31}$, $C_{17}H_{31}$, $C_{17}H_{33}$, $C_{17}H_{35}$, $C_{18}H_{37}$.

The data on the biological activity of these compounds are not available.

SUMMARY OF THE INVENTION

To provide new means effecting on microorganisms zinc or copper (II) salt of the general formula is proposed:

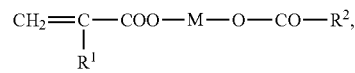

wherein M-Zn or Cu, $R^1$—H or $CH_3$, $R^2$—$C_2$-$C_{25}$ alkyl, excluding

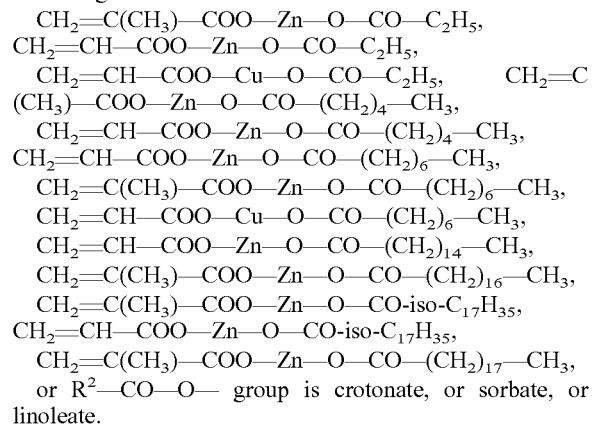

or $R^2$—CO—O— group is crotonate, or sorbate, or linoleate.

To solve the same problem it is also proposed to use zinc or copper (II) salt of the general formula

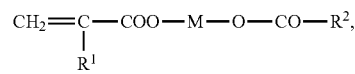

wherein M-Zn or Cu, $R^1$—H or $CH_3$, $R^2$—$C_2$-$C_{25}$ alkyl or $R^2$—CO—O— group is crotonate, or sorbate, or linoleate, as a biocide.

It was surprisingly found that zinc and copper (II) salts corresponding to the above formula along with bactericidal and fungicidal activities also exhibit high virucidal activity which ZMA substantially lacks.

DETAILED DESCRIPTION OF THE PREFERRED EMBODIMENTS

The essence of the invention is illustrated by examples given below. Examples 1-13 describe the preparation and properties of certain representatives of the proposed series of substances, examples 14-31 and 38-49—their virucidal activity. Examples 32-37 and 50 are comparative and illustrate substantial absence of virucidal activity of ZMA in conditions described in examples 14-31 and 38-49. Example 51 illustrates bactericidal activity and examples 52-66—fungicidal activity of representatives of the proposed series of substances.

Example 1

50 g of crotonic (2-butenoic) acid and 200 ml of distilled water are placed into a 500 ml round-bottom flask. Then a suspension of 46.76 g of zinc oxide in 100 ml of distilled water is gradually added to the solution under constant stirring, whereupon 41.86 g of acrylic acid is added, and the suspension is stirred until completely dissolving solids. The obtained solution is evaporated to dryness at temperature of not more than 70° C. and the resulted solid product is subjected to recrystallization from distilled water. 127 g of water-soluble powdered zinc acrylate-crotonate with melting point of 180° C. is obtained which corresponds to the above general formula wherein $R^1$=H, $R^2$=$C_3H_5$ (98.7% yield of the stoichiometric). The results of elemental analysis of salts obtained as described in this and subsequent examples are given in Table 1.

Example 2

Zinc methacrylate-butyrate ($R^1$=$CH_3$, $R^2$=$C_3H_7$) with melting point of 202° C. is obtained in 99% yield of the stoichiometric by analogy with Example 1 using methacrylic acid instead of acrylic one and butyric (butanoic) acid instead of crotonic one.

Example 3

Zinc acrylate-capronate ($R^1$=H, $R^2$=$C_5H_{11}$) with melting point of 185° C. is obtained in 98.4% yield of the stoichiometric by analogy with Example 1 using capronic (hexanoic) acid instead of crotonic one and heating acid suspension in water up to 175° C. until capronic acid is completely dissolved whereupon zinc oxide and subsequently acrylic acid are added.

Example 4

Copper acrylate-propionate ($R^1$=H, $R^2$=$C_2H_5$) with melting point of 185° C. is obtained in 99% yield of the stoichiometric by analogy with Example 1 using propionic (propanoic) acid instead of crotonic one and copper (II) oxide instead of zinc oxide.

Example 5

Copper methacrylate-valerate ($R^1$=$CH_3$, $R^2$=$C_4H_9$) with melting point of 185° C. is obtained in 95% yield of the stoichiometric by analogy with Example 3 using methacrylic acid instead of acrylic one, valerianic (pentanoic) acid instead of capronic one and copper (II) oxide instead of zinc oxide.

Example 6

Copper methacrylate-sorbate ($R^1$=$CH_3$, $R^2$=$C_5H_7$) with melting point of 220° C. is obtained in 93% yield of the stoichiometric by analogy with Example 3 using methacrylic acid instead of acrylic one, sorbic (2,4-hexadienoic) acid instead of capronic one and copper (II) oxide instead of zinc oxide.

Example 7

Copper acrylate-caprinate ($R^1$=H, $R^2$=$C_9H_{19}$) with melting point of 187° C. is obtained in 97.8% yield of the stoichiometric by analogy with Example 3 using capric (decanoic) acid instead of capronic one and copper (II) oxide instead of zinc oxide.

Example 8

Copper methacrylate-laurate ($R^1$=$CH_3$, $R^2$=$C_{11}H_{23}$) with melting point of 210° C. is obtained in 97% yield of the stoichiometric by analogy with Example 1 with the difference that the process is carried out in ether medium using methacrylic acid instead of acrylic one, lauric (dodecanoic) acid instead of capronic one and copper (II) oxide instead of zinc oxide.

Example 9

Zinc acrylate-undecylate ($R^1$=H, $R^2$=$C_{10}H_{21}$) with melting point of 177° C. is obtained in 95% yield of the stoichiometric by analogy with Example 8 using undecylic (undecanoic) acid instead of lauric one.

Example 10

Copper acrylate-stearate ($R^1$=H, $R^2$=$C_{17}H_{35}$) with melting point of 198° C. is obtained in 96% yield of the stoichiometric by analogy with Example 8 using stearic (octadecanoic) acid instead of lauric one and copper (II) oxide instead of zinc oxide.

Example 11

Zinc methacrylate-myristate ($R^1$=$CH_3$, $R^2$=$C_{13}H_{27}$) with melting point of 215° C. is obtained in 98% yield of the stoichiometric by analogy with Example 8 using methacrylic acid instead of acrylic one and myristic (tetradecanoic) acid instead of lauric one.

Example 12

Copper acrylate-linolenoate ($R^1$=H, $R^2$=$C_{17}H_{29}$) with melting point of 178° C. is obtained in 97% yield of the stoichiometric by analogy with Example 8 using linolenic (3,6,9-octadecatrienoic) acid instead of lauric one and copper (II) oxide instead of zinc oxide.

Example 13

Zinc acrylate-cerotinoate ($R^1$=H, $R^2$=$C_{25}H_{51}$) with melting point of 181° C. is obtained in 98% yield of the stoichiometric by analogy with Example 8 using cerotinic (hexacosanoic) acid instead of lauric one.

Examples 14-19

Virucidal activity of zinc acrylate-capronate obtained as described in Example 3 against human immunodeficiency virus (HIV) was investigated in suspension test in vitro according to the reference document "Guidelines for investigating and evaluating the virucidal activity of disinfectants" MU 3.52431-08 (approved on Dec. 13, 2008 by Service for Consumer Rights Protection and Human Health Control of the Russian Federation) at a concentration of biocide in an aqueous solution from 0.01 to 0.1 mass % and time of exposure from 30 to 60 min. The activity specified in the above document was estimated by the degree of inhibition of infectious virus titre measured as lg $TCID_{50}$ ($TCID_{50}$—50% tissue cytopathic infectious dose) which should not be less than 4 for a disinfectant. Test results for salts obtained as described in these and subsequent examples are given in Table 2.

Examples 20-25

Virucidal activity of copper acrylate-propionate obtained as described in example 4 was investigated by analogy with examples 14-19.

Examples 26-31

Virucidal activity of zinc methacrylate-myristate obtained as described in example 11 was investigated by analogy with examples 14-19.

Examples 32-37 (Comparative)

For comparison, virucidal activity of known biocide—zinc methacrylate-acetate (ZMA) against HIV was investigated by analogy with examples 14-19.

Examples 38-41

Virucidal activity of zinc methacrylate-butyrate obtained as described in example 2 against influenza A virus was investigated by analogy with examples 16-19 at a concentration of biocide in an aqueous solution from 0.05 to 0.1 mass %.

Examples 42-45

Virucidal activity of zinc acrylate-crotonate obtained as described in example 1 was investigated by analogy with examples 38-41.

Example 46-49

Virucidal activity of copper methacrylate-sorbate obtained as described in example 6 was investigated by analogy with examples 38-41.

Example 50 (Comparative)

For comparison, virucidal activity of known biocide—zinc methacrylate-acetate (ZMA) against influenza A virus was investigated by analogy with example 41 at a concentration of biocide in an aqueous solution of 0.1 mass % and time of exposure of 60 min.

As it follows from Table 2, the claimed compounds meet the criterion specified in the reference document for disinfectants in respect of two investigated test viruses while their closest structural analogue—ZMA—does not substantially exhibit virucidal activity against these viruses.

Example 51

Bactericidal activity of zinc acrylate-crotonate obtained as described in Example 1, copper acrylate-stearate obtained as described in Example 10 and copper methacrylate-sorbate obtained as described in Example 6 is determined according to the known method (RU 2378363, C12N 1/00, C12Q 1/00, 2010) based on the exposure of a bacterial culture in a solution of bactericidal substance for a certain period of time followed by its neutralization and inoculation of the culture on a solid nutrient medium. The sensitivity of microorganisms to a disinfectant is estimated by microorganism growth on the nutrient medium up to 300 CFU/ml (CFU—colony-forming unit) wherein growth up to 100 CFU/ml indicates incomplete bactericidal effect, growth up to 100-300 CFU/ml indicates sub-bactericidal effect and growth up to more than 300 CFU/ml indicates resistance of microorganisms to a disinfectant. The determination is performed on $E.\ coli$ No. 906 and $S.\ aureus$ No. 1257 test strains conventionally used to study the bactericidal activity of biocides as well as on clinical strain $P.\ aeruginosa$ at salt concentrations from 2 to 4% and time of exposure from 5 to 60 min. Test results are given in Table 3. It follows from Table 3 that zinc acrylate-crotonate and copper methacrylate-sorbate at concentration of 4.0% exhibit sustained bactericidal effect against all investigated strains at time of exposure from 15 min. Copper acrylate-stearate shows sustained bactericidal effect against two first strains at concentration of 2.0% and time of exposure of 60 min. as well as at concentration of 4.0% and time of exposure from 5 min. while its bactericidal effect against the third strain is exhibited at concentration of 4.0% and time of exposure of more than 30 min.

Examples 52-66

The fungicidal activity of the proposed salts is determined according to GOST 30028.4-2006 by testing samples of various materials treated with these salts for resistance to fungal spores. Test results in terms of tolerance time (in days) are given in Table 4 wherein tolerance time for untreated materials are given for comparison.

INDUSTRIAL APPLICABILITY

The present invention can be used for production of biocides intended for combating pathogenic microorganisms, for example, for incorporation into disinfecting and antiseptic compositions, polymer materials, for treatment of wood, paper, building structures and other materials to prevent their damage caused by biological matters (microorganisms, fungi, algae), manufacture of various articles with biocidal properties, etc.

TABLE 1

Results of elemental analysis of salts

| Example 1 | Name 2 | Empirical formula 3 | Sample weight, g 4 | C, g calculated 5 | C, g determined 6 | H, g calculated 7 | H, g determined 8 | Zn, g calculated 9 | Zn, g determined 10 | Cu, g calculated 11 | Cu, g determined 12 |
|---|---|---|---|---|---|---|---|---|---|---|---|
| 1 | Zinc acrylate-crotonate | $C_7H_8O_4Zn$ | 0.5 | 0.1903 | 0.2<br>0.1899 | 0.0204 | 0.02 | 0.148 | 0.149<br>0.148 | | |
| 2 | Zinc methacrylate-butyrate | $C_8H_{12}O_4Zn$ | 0.5 | 0.2029 | 0.203<br>0.202 | 0.0254 | 0.025<br>0.026 | 0.1364 | 0.137 | | |

TABLE 1-continued

Results of elemental analysis of salts

| Example 1 | Name 2 | Empirical formula 3 | Sample weight, g 4 | C, g calculated 5 | C, g determined 6 | H, g calculated 7 | H, g determined 8 | Zn, g calculated 9 | Zn, g determined 10 | Cu, g calculated 11 | Cu, g determined 12 |
|---|---|---|---|---|---|---|---|---|---|---|---|
| 3 | Zinc acrylate-capronate | $C_9H_{14}O_4Zn$ | 0.5 | 0.2138 | 0.2137 0.2139 | 0.0277 | 0.0278 0.0276 | 0.129 | 0.129 | | |
| 4 | Copper acrylate-propionate | $C_6H_8O_4Cu$ | 0.5 | 0.1726 | 0.1726 0.1728 | 0.0192 | 0.019 0.02 | | | 0.1524 | 0.1525 |
| 5 | Copper methacrylate-valerate | $C_9H_{14}O_4Cu$ | 0.5 | 0.216 | 0.218 0.216 | 0.028 | 0.029 0.027 | | | 0.127 | 0.128 |
| 6 | Copper methacrylate-sorbate | $C_{10}H_{12}O_4Cu$ | 0.5 | 0.231 | 0.229 0.23 | 0.023 | 0.024 0.023 | | | 0.122 | 0.123 |
| 7 | Copper acrylate-caprinate | $C_{13}H_{22}O_4Cu$ | 0.5 | 0.255 | 0.256 0.255 | 0.0376 | 0.0377 | | | 0.104 | 0.105 |
| 8 | Copper methacrylate-laurate | $C_{16}H_{28}O_4Cu$ | 0.5 | 0.1558 | 0.156 0.155 | 0.013 | 0.0129 0.0133 | | | 0.0913 | 0.092 |
| 9 | Zinc acrylate-undecylate | $C_{14}H_{24}O_4Zn$ | 0.5 | 0.2618 | 0.262 0.2617 | 0.0374 | 0.0375 0.0374 | 0.1005 | 0.1 0.1006 | | |
| 10 | Copper acrylate-stearate | $C_{21}H_{38}O_4Cu$ | 0.5 | 0.302 | 0.303 | 0.046 | 0.045 0.046 | | | 0.076 | 0.077 |
| 11 | Zinc methacrylate-myristate | $C_{18}H_{32}O_4Zn$ | 0.5 | 0.271 | 0.27 | 0.042 | 0.043 | 0.0856 | 0.0855 | | |
| 12 | Copper acrylate-linolenoate | $C_{21}H_{32}O_4Cu$ | 0.5 | 0.306 | 0.31 0.305 | 0.0389 | 0.039 | | | 0.077 | 0.078 |
| 13 | Zinc acrylate-cerotinoate | $C_{29}H_{54}O_4Zn$ | 0.5 | 0.327 | 0.328 0.327 | 0.051 | 0.05 | 0.061 | 0.06 0.062 | | |

TABLE 2

Results of investigation of virucidal activity of salts

| Example | Biocide | Concentration of biocide in a solution, % | Virus | Time of exposure, min. | Degree of virus inhibition, lg $TCID_{50}$ |
|---|---|---|---|---|---|
| 14 | Zinc | 0.01 | HIV | 30 | 0.0 |
| 15 | acrylate- | 0.01 | HIV | 60 | 0.0 |
| 16 | capronate | 0.05 | HIV | 30 | 2.0 |
| 17 | | 0.05 | HIV | 60 | 3.5 |
| 18 | | 0.1 | HIV | 30 | 4.5 |
| 19 | | 0.1 | HIV | 60 | 5.0 |
| 20 | Copper | 0.01 | HIV | 30 | 0.0 |
| 21 | acrylate- | 0.01 | HIV | 60 | 1.0 |
| 22 | propionate | 0.05 | HIV | 30 | 3.0 |
| 23 | | 0.05 | HIV | 60 | 3.5 |
| 24 | | 0.1 | HIV | 30 | 4.0 |
| 25 | | 0.1 | HIV | 60 | 5.0 |
| 26 | Zinc | 0.01 | HIV | 30 | 0.5 |
| 27 | methacrylate- | 0.01 | HIV | 60 | 1.5 |
| 28 | myristate | 0.05 | HIV | 30 | 3.0 |
| 29 | | 0.05 | HIV | 60 | 4.5 |
| 30 | | 0.1 | HIV | 30 | 5.5 |
| 31 | | 0.1 | HIV | 60 | 6.5 |
| 32 (compar.) | Zinc | 0.01 | HIV | 30 | 0.0 |
| 33 (compar.) | methacrylate- | 0.01 | HIV | 60 | 0.0 |
| 34 (compar.) | acetate | 0.05 | HIV | 30 | 0.0 |
| 35 (compar.) | | 0.05 | HIV | 60 | 0.0 |
| 36 (compar.) | | 0.1 | HIV | 30 | 1.0 |
| 37 (compar.) | | 0.1 | HIV | 60 | 2.5 |
| 38 | Zinc | 0.05 | Influenza A | 30 | 4.0 |
| 39 | methacrylate- | 0.05 | Influenza A | 60 | 4.8 |
| 40 | butyrate | 0.1 | Influenza A | 30 | 4.5 |
| 41 | | 0.1 | Influenza A | 60 | 5.1 |
| 42 | Zinc | 0.05 | Influenza A | 30 | 3.8 |
| 43 | acrylate- | 0.05 | Influenza A | 60 | 4.5 |
| 44 | crotonate | 0.1 | Influenza A | 30 | 4.2 |
| 45 | | 0.1 | Influenza A | 60 | 4.9 |
| 46 | Copper | 0.05 | Influenza A | 30 | 4.1 |
| 47 | methacrylate- | 0.05 | Influenza A | 60 | 4.8 |
| 48 | sorbate | 0.1 | Influenza A | 30 | 4.7 |
| 49 | | 0.1 | Influenza A | 60 | 5.2 |

TABLE 2-continued

Results of investigation of virucidal activity of salts

| Example | Biocide | Concentration of biocide in a solution, % | Virus | Time of exposure, min. | Degree of virus inhibition, lg TCID$_{50}$ |
|---|---|---|---|---|---|
| 50 (compar.) | Zinc methacrylate-acetate | 0.1 | Influenza A | 60 | 0.0 |

TABLE 3

Bactericidal activity of salts

| Concentration, wt % | Time of exposure, min. | Zinc acrylate-crotonate | | | Copper acrylate-stearate | | | Copper methacrylate-sorbate | |
|---|---|---|---|---|---|---|---|---|---|
| | | E. coli 906 | S. aureus 1257 | P. aeruginosa | E. coli 906 | S. aureus 1257 | P. aeruginosa | E. coli 906 | S. aureus 1257 |
| 4.0 | 60 | NG | NG | NG | NG | NG | NG | NG | NG |
| | | NG | NG | NG | NG | NG | NG | NG | NG |
| | | | | | NG | NG | NG | NG | NG |
| | | | | | NG | NG | NG | NG | NG |
| | 30 | NG | NG | NG | NG | NG | NG | NG | NG |
| | | NG | NG | NG | NG | NG | NG | NG | NG |
| | | | | | NG | NG | >300 CFU | NG | NG |
| | | | | | | | | | NG |
| | 15 | NG | NG | NG | NG | NG | >300 CFU | NG | NG |
| | 5 | NG | 7 CFU | 1 CFU | NG | NG | CG | 1 CFU | NG |
| 2.0 | 60 | 1 CFU | >300 CFU | NG | NG | NG | CG | 5 CFU | 1 CFU |
| | | 3 CFU | >300 CFU | 3 CFU | NG | NG | | 4 CFU | 3 CFU |
| | | | | | NG | NG | | | |
| | 30 | >300 CFU | CG | 4 CFU | 10 CFU | 25 CFU | CG | 45 CFU | 35 CFU |
| | | | | | | | | 53 CFU | 43 CFU |
| | 15 | 42 CFU | CG | 10 CFU | 100 CFU | >300 CFU | CG | 78 CFU | 85 CFU |
| | 5 | 75 CFU | CG | >300 CFU | CG | CG | CG | >300 CFU | >300 CFU |

Note:
NG—no growth;
CFU—number of colony-forming units in 1 ml;
CG—confluent growth

TABLE 4

Fungicidal activity of salts

| Example No. | Test material | Additive Name | Content, wt % | Tolerance time, days |
|---|---|---|---|---|
| 52 | Emulsion polyvinyl chloride | Zinc acrylate-undecylate | 5 | 10 |
| 53 | Emulsion polyvinyl chloride | Copper methacrylate-valerate | 5 | 16 |
| 54 | Emulsion polyvinyl chloride | Copper acrylate-stearate | 5 | 12 |
| 55 | Emulsion polyvinyl chloride | Zinc methacrylate-butyrate | 5 | 11 |
| 56 | Emulsion polyvinyl chloride | Copper acrylate-caprinate | 5 | 20 |
| 57 | Emulsion polyvinyl chloride | Zinc methacrylate-myristate | 5 | 12 |
| 58 | Emulsion polyvinyl chloride | Control test | — | 6 |
| 59 | Paper impregnated with latex SKS 65 GP | Zinc methacrylate-butyrate | 5 | 10 |
| 60 | Paper impregnated with latex SKS 65 GP | Copper acrylate-stearate | 5 | 16 |
| 61 | Paper impregnated with latex SKS 65 GP | Zinc acrylate-undecylate | 5 | 12 |

TABLE 4-continued

Fungicidal activity of salts

| Example No. | Test material | Additive Name | Content, wt % | Tolerance time, days |
|---|---|---|---|---|
| 62 | Paper impregnated with latex SKS 65 GP | Copper acrylate-caprinate | 5 | 19 |
| 63 | Paper impregnated with latex SKS 65 GP | Control test | — | 4 |
| 64 | Paper impregnated with petrolatum base | Zinc acrylate-undecylate | 4.7 | 20 |
| 65 | Paper impregnated with petrolatum base | Copper acrylate-caprinate | 5 | 21 |
| 66 | Paper impregnated with petrolatum base | Control test | — | 15 |

What is claimed is:

1. A method of using a zinc or copper (II) salt of the general formula:

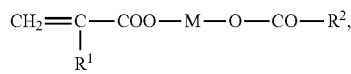

as a virucide, the method comprising dissolving the zinc or copper (II) salt in an aqueous medium to form a solution having a salt concentration in a range from 0.01% to 0.1%, and treating a material with the solution, wherein in the general formula M is Zn or Cu, $R^1$ is H or $CH_3$, $R^2$ is a $C_2$-$C_{25}$ alkyl, or $R^2$—CO—O— is selected from the group consisting of crotonate, sorbate, and linoleate.

2. A method of using a zinc or copper (II) salt of the general formula:

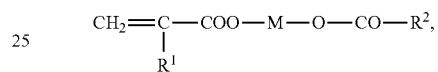

as a bactericide, the method comprising dissolving the zinc or copper (II) salt in an aqueous medium to form a solution having a salt concentration in a range from 2% to 4%, and treating a material with the solution, wherein in the general formula M is Zn or Cu, $R^1$ is H or $CH_3$, $R^2$ is a $C_2$-$C_{25}$ alkyl, or $R^2$—CO—O— is selected from the group consisting of crotonate, sorbate, and linoleate.

* * * * *